United States Patent [19]  
Fisher et al.

[11] Patent Number: 4,906,645  
[45] Date of Patent: Mar. 6, 1990

[54] PYRIDYL AMINOETHANOL COMPOUNDS WITH GROWTH PROMOTION AND AN INCREASE IN FEED EFFICIENCY

[75] Inventors: Michael H. Fisher, Ringoes; Matthew J. Wyvratt, Mountainside, both of N.J.

[73] Assignee: Merck & Co., Inc., Rahway, N.J.

[21] Appl. No.: 242,859

[22] Filed: Sep. 12, 1988

[51] Int. Cl.$^4$ ............................................. A61K 31/44
[52] U.S. Cl. ...................................... 514/352; 546/312
[58] Field of Search ........................ 546/312; 514/352; 544/252

[56] References Cited

U.S. PATENT DOCUMENTS 4,358,455 11/1982 Atkinson et al. ................... 546/312  
4,761,421 8/1988 Muir ..................................... 514/352

Primary Examiner—Mary C. Lee  
Assistant Examiner—Zinna Northington-Davis  
Attorney, Agent, or Firm—David L. Rose; Hesna J. Pfeiffer

[57] ABSTRACT

There are disclosed six pyridyl aminoethanol substituted on the amine with a substituted phenylalkyl group. The compounds are highly potent growth promotion agents for animals and compositions for such uses are also disclosed.

7 Claims, No Drawings

PYRIDYL AMINOETHANOL COMPOUNDS WITH GROWTH PROMOTION AND AN INCREASE IN FEED EFFICIENCY

BACKGROUND OF THE INVENTION

U.S. Pat. No. 4,358,455 discloses heterocyclic aminoethanol compounds which are useful as cardiovascular agents. The generic disclosure of that patent encompasses the six compounds of this invention, however, there is no specific disclosure of the instant six compounds. It has been discovered that the compounds of this invention have a surprisingly and unexpectedly high level of activity and safety as growth promotion agents when compared to the disclosed compounds closest in structure to the instant six compounds. In addition, U.S. 4,761,421 discloses the use of one compound within the scope of 4,358,455 which has growth promotion activity, however, the instant compounds have a substantially higher margin of safety than this single compound.

SUMMARY OF THE INVENTION

This invention is concerned with six compounds which have been found to have a surprisingly high level of animal growth promotion activity and a higher margin of safety when compared to closely related compounds. Thus it is an object of this invention to describe such compounds. A further object of this invention is to describe the growth promotion uses of such compounds. A still further object is to describe compositions using one or more of the six compounds as the active ingredient thereof. Further objects will become apparent from a reading of the following description.

DESCRIPTION OF THE INVENTION

The compounds of this invention are best described in the following structural formula:

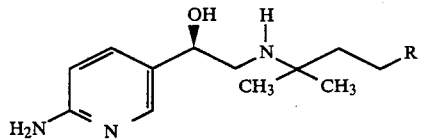

wherein R is

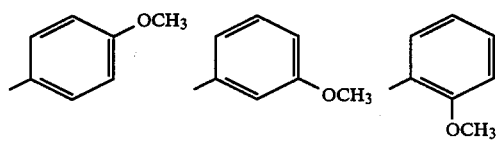

The compounds of this invention have one chiral center at the carbon atom of the ethanolamine bearing the hydroxy group. The chiral center confers optical activity on the compounds.

Individual enantiomers are commonly designated according to the optical rotation they effect by the symbols (+) and (−), (L) and (D), (l) and (d) or combinations thereof. These isomers may also be designated according to their absolute spatial configuration by (S) and (R), which stands for sinister and rectus, respectively.

The individual optical isomers may be prepared using conventional resolution procedures, e.g., treatment with an appropriate optically active acid, separating the diastereomers and then recovering the desired R-isomer. Alternatively, the enantiomers may be separated on a chromatographic column containing an optically active support. In addition, the individual optical isomers may be prepared by asymmetric synethesis. For example, the a symmetric center in the ethanolamine chain may be controlled by using a chiral reducing agent such as (R)-Alpine borane.

The R-stereochemistry at the 1-position of the ethanolamine group has been found to be particularly advantageous in the compounds of this invention. The R-stereochemistry is used to designate the hydroxy group as being above the plane of the instant compounds as shown in the foregoing structural formula.

The R-isomer (with the hydroxy group above the molecular plane) is unexpectedly and significantly more active than the S-isomer (with the hydroxy group below the plane) when the instant compounds are used as growth promotor agents. Thus the instant invention is directed to the R-stereoisomer significantly free of the S-isomer which offer the advantage of a compound possessing activity at a level many multiples that of the S-isomer and the added benefit that with a single, substantially pure isomer, drug residues, always a concern to regulatory agencies which consider the safety and efficiency of an animal health drug prior to its commercial release, will be significantly reduced from that of the racemic mixture. The compounds of this invention are prepared according to the following reacton scheme:

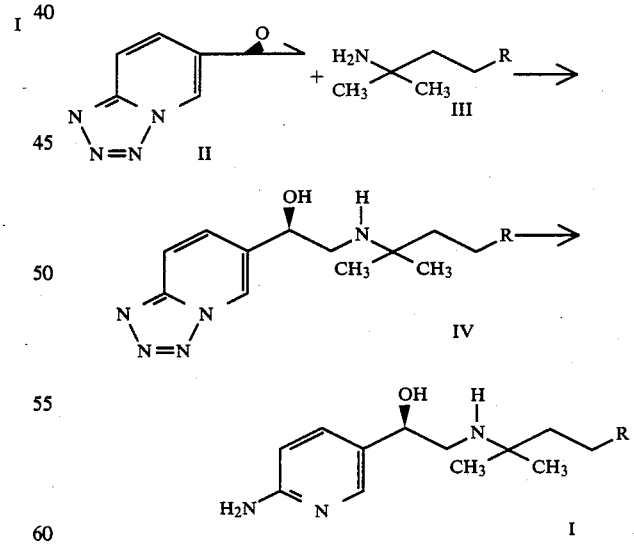

In the foregoing reaction scheme Compound II is prepared according to the procedures described in U.S. Pat. No. 4358455. Compound II, if prepared using stereo specific reducing agents, will itself be a single optical isomer. Compound II is reacted with an excess of amine III in order to prepare Compound IV. The reaction is generally carried out at from 50° C. to the reflux temperature in an appropriate solvent. The reaction is complete in from 1 to 24 hours.

Compound IV is treated with tin (II) chloride in an alcohol solvent such as methanol, optionally in the presence of one equivalent of hydrogen chloride. The reaction is carried out at from 50° C. to reflux, preferably at reflux temperature, and is generally complete in from 1 to 24 hours.

The amine starting materials are prepared by the methylation of the appropriately substituted butane-2-one or the Grignard reaction of the phenethyl bromide with acetone followed by amination as shown in the following reaction scheme:

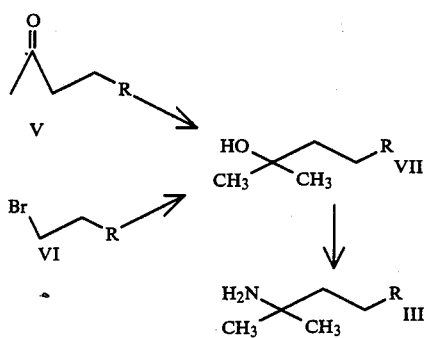

Compound V is methylated using the Grignard reagent methyl magnesium iodide under the standard Grignard reaction conditions of a dry ether solution carried out at from 0° C. to room temperature. Compound VII is isolated using normal techniques known to those skilled in the art. Compound VII may also be prepared by preparing the Grignard reagent of Compound VI and reacting it with acetone under similar reaction conditions as described above.

Compound VII is aminated to form Compound III. The reaction is carried out by the in situ preparation of the formamide prepared by treating Compound VII with an alkali metal by cyanide in the presence of a strong acid such as sulfuric acid. The reaction is carried out at from room temperature to 100° C., preferrably about 50° C. and is complete in from ½ to 24 hours. The formamide is hydrolized to the amine III with hydrochloric acid. The reaction is carried out at from 50° C. to reflux and is completed in from ½ to 6 hours. The products are isolated using standard techniques.

The compounds of this invention are capable of forming salts with various inorganic and organic acids and such salts are also within the scope of this invention. Typical acids are hydrochloric, hydrobromic, sulfuric, phosphoric, methanesulfonic, toluenesulfonic, maleic, fumaric, camphorsulfonic and the like. The non-toxic physiologically acceptable salts are preferred, although other salts are also useful, such as in isolating or purifying the product.

The salts may be formed by conventional means, such as by reacting the free base form of the product with one or more equivalents of the appropriate acid in a solvent or medium in which the salt is insoluble, or in a solvent such as water which is removed in vacuo or by freeze drying or by exchanging the anions of an existing salt for another anion on a suitable ion exchange resin.

The compounds of this invention are useful as animal growth promotants. They can be used to increase the growth and feed efficiency of ruminant and non-ruminant animals such as sheep, cattle, goats, horses, swine, chickens and the like. The active compound can be fed to the animal by incorporating it into the animal's feed or drinking water or it can be administered in a unit dosage form either orally as a drench, tablet, bolus or sustained release bolus or parenterally by injection or from a subcutaneous implant. The administration of the active compounds will produce a surprising increase in body weight, decrease in body fat and increase in body protein for the same food intake.

The active compounds can be administered to the animals at daily rates of from 0.001 to 10 mg/kg of body weight which may vary depending upon the particular animal being treated as well as the age and general physical condition of the animal. Preferably, daily dosages of from 0.01 to 1.0 mg/kg are utilized. When administered as part of the animal's feed or drinking water, the active compound is present at rates of from 0.01 to 100 ppm which is determined to provide the appropriate daily amounts of the growth promotant compound.

At the same dosages listed above for growth promotion effects, substantial increases in feed efficiency are also observed.

The following examples are presented in order that the invention might be more fully understood. They should not be considered as limitative of the invention.

EXAMPLE 1

2-Amino-2-methyl-4-(4-methoxyphenyl)-butane

To a cold solution (0° C.) of methyl magnesium iodide (11 ml of commercial 3.0 M etheral solution) in 70 ml of anhydrous ether, a solution of 4-(4-methoxyphenyl)butan-2-one (5.5 g) in 50 ml of ether was added dropwise under nitrogen. The reaction mixture was permitted to slowly warm to room temperature overnight. The mixture was cooled with ice and quenched with cold 2 N $H_2SO_4$ (100 ml). The layers were separated and the aqueous solution further extracted with ether. The combined organic layers were washed with 5% $NaHCO_3$ solution, water and brine and then dried with anhydrous sodium sulfate. Concentration afforded 5.6 g of alcohol product. A solution of this material (5.07 g) in 5 ml of glacial acetic acid was added slowly to a solution of 1.8 g of KCN and 1.6 ml of concentrated sulfuric acid in 7 ml of acetic acid (exothermic). The reaction mixture was then heated on a water bath to 50° C. for 1 hour. TLC of the reaction mixture still indicated starting alcohol and olefin. Additional equivalents of KCN (1.8 g) and $H_2SO_4$ (1.6 ml) were added until the reaction appeared complete by TLC. The reaction mixture was poured onto ice/water and the mixture neutralized with 5N NaOH. The resulting mixture was repeatedly extracted with ether. The combined extracts were washed with water and brine, dried with anhydrous magnesium sulfate and concentrated to give 4.95 g of formamide. This material was chromatographed on silica gel (95:5 $CH_2Cl_2$:MeOH) to give 2.75 g of purified formamide. This material was placed in 25 ml of 6N HCl and the resulting mixture heated at reflux for 1 hour and then stirred overnight. The aqueous mixture was extracted with ether and then treated with 50% NaOH solution until pH =11. The aqueous layer was repeatedly extracted with ether. These etheral extracts were washed with water and brine and then dried with sodium sulfate. Concentration gave 2.2 g of the titled amine.

EXAMPLE 2

(R)-a-[[(1,1-Dimethyl-3-(4-methoxyphenyl)propyl-)amino]methyl]tetrazolo[1,5-a]pyridine-6-methanol A solution of 509 mg (3.13 mmol) of (R)-2-(tetrazolo[1,5-a]pyrid-6-yl)oxirane and 619 mg (3.21 mmol) of 2-amino-2-methyl-4-(4-methoxyphenyl)butane in 25 ml of absolute ethanol was heated at reflux for two hours and then stirred overnight at room temperature. The reaction mixture was concentrated and the residue chromatographed on silica gel (4:1:2 ethyl acetate:n-propanol:water with 1% NH4OH) to give 497 mg of product. Recrystallization from isopropanol afforded 357 mg of crystalline tetrazole, mp. 139–40° C.

EXAMPLE 3

(R)-6-Amino-a-[[(1,1-dimethyl-3-(4-methoxyphenyl)propyl)amino]methyl]-3-pryridinemethanol dihydrochloride A solution of 357 mg (1.08 mmol) of (R)-a-[[(1,1-dimethyl-3-(4-methoxyphenyl)propyl)amino]methyl]-tetrazolo[1,5-a]pyridine-6-methanol and 465 mg (2.01 mmol) of SnCl$_2$·2H$_2$O in 25 ml of methanol was heated at reflux for one day. The reaction mixture was concentrated and the residue partitioned between methylene chloride and 2N NaOH. The layers were separated and the aqueous portion repeatedly extracted with methylene chloride. The combined organic extracts were backwashed with brine and then dried with anhydrous sodium sulfate. Concentration and chromatography on silica gel (4:1:2 ethyl acetate:n-propanol:water with 0.5% NH4OH) gave 142 mg of pure product. The dihydrochloride salt was prepared with HCl in ethanol, mp. 186–88°C.; $[a]_{25°D} = -28°$ (MeOH).

EXAMPLE 4

2-Amino-2-methyl-4-(3-methoxyphenyl)butane

To a cold solution of 3-methoxyphenethyl alcohol (7.55 g, 50 mmol) in 20 ml of dry (sieves) methylene chloride, a solution of phosphorus tribromide (7 g, 26 mmol) in 20 ml of methylene chloride was slowly added under nitrogen. The reaction mixture was permitted to warm to ambient temperature overnight. The reaction was then quenched in ice/water slowly and the resulting solution neutralized with 5N NaOH and then extracted with methylene chloride. The combined extracts were washed with water and brine, dried with anhydrous magnesium sulfate and concentrated to give 7.3 g of 3-methoxyphenethyl bromide. A solution of this bromide (7.3 g) in 10 ml of dry tetrahydrofuran (THF) was slowly added to a flask containing magnesium chips (1.03 g) and a small crystal of iodine in 30 ml of THF. The reaction mixture was then heated to reflux for 1 hour. To this mixture which was cooled with ice, a solution of dry acetone (2.2 g) in 10 ml of dry THF was added and the reaction mixture stirred at ambient temperature overnight. The mixture was quenched (0° C.) with a cold solution of NH4Cl followed by 1N HCl. The mixture was extracted with ethyl acetate and dried with anhydrous magnesium sulfate. Concentration and chromatography on silica gel (10-30% ethyl acetate in hexanes) afforded 2.31 g of carbinol. This carbinol (2.3 g) in 4 ml of glacial acetic acid was slowly added to a solution of KCN (2.36 g) and H$_2$SO$_4$ (3.63 g) in 15 ml of acetic acid. The reaction mixture was then stirred at 90° C. (bath temperature) overnight under nitrogen. Additional KCN (3.28 g), H$_2$SO$_4$ (8 ml in 24 ml of acetic acid) and acetic acid (18 ml) were added and the reaction mixture heated overnight. The reaction was quenched by pouring the reaction mixture into ice/water and adjusting the pH of the solution to neutrality with 5N NaOH. The solution was repeatedly extracted with ethyl acetate and the combined extracts backwashed with water and brine and then dried with anhydrous sodium sulfate. Concentration afforded 1.64 g of formamide which was hydrolyzed to the amine in 6N HCl (40 ml) at reflux for 3 hours. The reaction mixture was partially concentrated, diluted with water and the pH of the solution adjusted with 5N NaOH to 12. The solution was extracted with ethyl acetate and the combined extracts backwashed with brine and dried with anhydrous sodium sulfate. Concentration gave 1.2 g of the titled amine.

EXAMPLE 5

(R)-a-[[(1,1-Dimethyl-3-(3-methoxyphenyl)propyl-)amino]methyl]tetrazolo[1,5-a]pyridine-6-methanol A solution of 1.02 g (6.3 mmol) of (R)-2-(tetrazolo[1,5-a]pyrid-6-yl)oxirane and 2-amino-2-methyl-4-(3-methoxyphenyl)butane (1.2 g, 6.26 mmol) in 40 ml of absolute ethanol was heated at reflux for 8 hours and then stirred at ambient temperature overnight. The reaction mixture was concentrated and chromatographed on silica gel (ethyl acetate) to afford 1.05 g of tetrazole product.

EXAMPLE 6

(R)-6-Amino-a-[[(1,1-dimethyl-3-(3-methoxyphenyl)propyl)amino]methyl]-3-pyridinemethanol dihydrochloride A solution of (R)-a-[[(1,1-dimethyl-3-(3-methoxyphenyl) propyl)amino]methyl]tetrazolo[1,5-a]pyridine-6-methanol (1.05 g, 2.94 mmol) in 35 ml of methanol was treated with SnCl$_2$·2H$_2$O (1.33 g, 5.9 mmol) and the resulting mixture heated at reflux for 24 hours under nitrogen. The reaction mixture was poured into a cold NaOH solution. The alkaline solution was repeatedly extracted with methylene chloride. The combined extracts were backwashed with brine and dried with anhydrous sodium sulfate. Concentration and then chromatography on silica gel (ethyl acetate then 4:1:2 ethyl acetate:n-propanol: water with 1% NH4OH) gave 665 mg of product. This material was dissolved in isopropanol and treated with a saturated ethanoloic solution of HCl. The acidic solution was diluted with ether and the resulting precipitate collected by filtration and dried in vacuo to give 606 mg of the dihydrochloride salt; mp. 190-2° C. (dec); $[a]_{25°D} = -30.6°$ (c =0.3, methanol);

Analysis: C$_{19}$H$_{27}$N$_3$O$_2$·2HCl:

Calcd: C, 56.72; H, 7.26; N, 10.41; Cl, 17.62.

Found: C, 56.12; H, 7.18; N, 10.19; Cl, 18.10.

EXAMPLE 7

2-Amino-2-methyl-4-(2-methoxyphenyl)butane

To cold (0° C.) neat 2-methoxyphenethyl alcohol (7.55 g, 49.6 mmol) under nitrogen, phosphorus tribromide (2.47 ml, 25.8 mmol) was added slowly. After the addition, the reaction mixture was permitted to warm to room temperature overnight and then quenched into ice water. The pH of the mixture was adjusted to 12 with 4N NaOH and extracted repeatedly with methylene chloride. The combined extracts were washed with brine and dried over anhydrous magnesium sulfate.

Concentration gave 7.22 g of an oil which was distilled at 115–17° C./4 mm to afford 4.94 of pure bromide. A solution of this bromide (3.96 g, 18.4 mmol) in 20 ml of tetrahydrofuran (THF) was slowly added to a mixture of magnesium (550 mg, 22.6 mmol) in THF (20 ml) containing a small crystal of iodine. The reaction mixture was heated at 60° C. for 1 hour and then cooled with ice. To this cold solution of grignard reagent, dry acetone (1.2 g, 20 mmol) in 15 ml of THF was slowly added. The reaction mixture was permitted to come to room temperature over two hours. The reaction mixture was cooled and quenched with saturated $NH_4OH$ solution with 1M HCl. The aqueous mixture was extracted with ether and the combined etheral layers backwashed with water and brine. The organic solution was dried with anhydrous sodium sulfate and concentrated to give 2.9 g of an oil which was chromatographed on silica gel (5% ethyl acetate in hexanes) to afford 1.01 g of carbinol. A solution of this carbinol (1.01 g, 5.18 mmol) in 2 ml of glacial acetic acid was added dropwise to a solution of KCN (675 mg, 10.4 mmol) and $H_2SO_4$ (0.56 ml, 10.57 mmol) in 6 ml of acetic acid. The reaction mixture was heated at 70° C. for one hour. Additional portions of KCN (675 mg) and $H_2SO_4$ (0.56 ml) were added until reaction was complete. The reaction mixture was poured onto ice water and the pH of the solution adjusted to neutrality with 5N NaOH. The aqueous solution was then extracted repeatedly with ether. The combined extracts were backwashed with brine and then dried with anhydrous magnesium sulfate. Concentration afforded 1.05 g of crude formamide. This material was treated with 20 ml of 6N HCl at reflux for 2 hours and then partially concentrated. The pH of this solution was adjusted to 11 with 5N NaOH and extracted with methylene chloride. The combined extracts were washed with brine, dried with anhydrous sodium sulfate and concentrated. The residue was chromatographed on silica gel (95:5:1 $CH_2Cl_2$:MeOH:$NH_4OH$) to give 561 mg of pure amine.

EXAMPLE 8

(R)-a-[[1,1-Dimethyl-3-(2-methoxyphenyl)propyl)amino]methyl]tetrazolo[1,5-a]pyridine-6-methanol A solution of 504 mg (3.11 mmol) of (R)-2-(tetrazolo[1,5-a]pyrid-6-yl)oxirane and 561 mg of 2-amino-2-methyl-4-(2-methoxyphenyl)butane in 25 ml of absolute ethanol was heated at reflux for 5 hours. The reaction mixture was concentrated and the residue chromatographed on silica gel (ethyl acetate) to give 715 mg of product.

EXAMPLE 9

(R)-6-Amino-a-[[(1,1-dimethyl-3-(2-methoxyphenyl)propyl)amino]methyl]-3-pyridinemethanol A solution of (R)-a-[[(1,1-dimethyl-3-(2-methoxyphenyl)propyl)amino]methyl]tetrazolo[1,5a]pyridine-6-methanol (715 mg, 2.01 mmol) and $SnCl_2 \cdot H_2O$ (907 mg, 4.02 mmol) in 25 ml of methanol was heated at reflux for 20 hours. The reaction mixture was poured into a solution of ice-water made basic with 2N NaOH. The mixture was repeatedly extracted with methylene chloride and the combined extracts backwashed with brine. The organic solution was dried with anhydrous sodium sulfate and concentrated to give 775 mg of crude product. This material was chromatographed on silica gel (4:1:2:1 ethyl acetate:n-propanol:water:$NH_4OH$) to afford 479 mg of pure product which was converted with ethanolic HCl to its hydrochoride salt, 342 mg, mp. 152–5° C.; $[a]_{25°D} = -26.9°$ (c =0.24, MeOH).

Analysis: $C_{19}H_{27}N_3O_2 \cdot 2HCl$:
Calcd: C, 56.72; H, 7.26; N, 10.44; Cl, 17.62.
Found: C, 56.64; H, 7.43; N, 10.31; Cl, 17.59.

EXAMPLE 10

2-Amino-2-methyl-4-(4-hydroxyphenyl)butane Hydrochloride

To a cold (0° C.) solution of methylmagnesium iodide (13.5 ml of 3M commercial solution) in 80 ml of anhydrous ether under nitrogen, a solution of 4-(4-tert-butyldimethylsilyloxyphenyl)butan-2-one(10 g, 36 mmol) in ether (50 ml) was added dropwise over one hour. The reaction mixture was stirred at room temperature overnight and then poured onto ice-water and the pH adjusted to neutrality with cold dilute HCl. The mixture was extracted with ether and the combined extracts washed with 5% $NaHCO_3$ solution and brine. The etheral solution was dried with anhydrous sodium sulfate and concentrated to give 10.2 g of carbinol. A solution of this material (10.2 g, 34 mmol) in 20 ml of glacial acetic acid was slowly added to a solution of KCN (4.53 g, 70.8 mmol) and $H_2SO_4$ (3.77 ml, 70.9 mmol) in 20 ml of acetic acid. The reaction mixture was then heated at 70° C. under nitrogen for 12 hours. Additional equivalents of KCN and $H_2SO_4$ were added until the reaction was complete by TLC. The reaction mixture was poured onto ice/water and the pH of the solution adjusted to neutrality with 50% NaOH. The aqueous solution was repeatedly extracted with ethyl acetate. The combined organic extracts were washed with brine and dried with anhydrous sodium sulfate. Concentration gave 8.74 g of crude product which was chromatographed on silica gel (95:5:1 $CH_2Cl_2$:MeOH:$NH_4OH$) to give 2.63 g of desilylated formamide. This material was treated with 40 ml of 6N HCl and heated at reflux for 4 hours under nitrogen. The reaction mixture was extracted with ethyl acetate. The aqueous phase was then concentrated partially and cooled in ice. The precipitate was collected by filtration and dried to give the amine hydrochloride, 999 mg.

EXAMPLE 11

(R)-a-[[(1,1-Dimethyl-3-(4-hydroxyphenyl)propyl)amino]methyl]tetrazolo[1,5-a]pyridine-6-methanol A solution of 527 mg (3.25 mmol) of (R)-2-tetrazolo[1,5-a]pyrid-6-yl)oxirane, 701 mg (3.25 mmol) of 2-amino-2-methyl-4-(4-hydroxyphenyl)butane hydrochloride and 300 mg of $NaHCO_3$ in 40 ml of absolute ethanol was heated at reflux for 10 hours. The reaction mixture was concentrated and chromatographed on silica gel (4:1:2:1 ethyl acetate:n-propanol:water:ammonium hydroxide) to give 605 mg of product.

EXAMPLE 12

(R)-6-Amino-a-[[(1,1-dimethyl-3-(4-hydroxyphenyl)propyl)amino]methyl]-3-pyridinemethanol dihydrochloride A solution of 595 mg (1.74 mmol) of (R)-a-[[(1,1-dimethyl-3-(4-hydroxyphenyl)propyl)amino]methyl]-tetrazolo[1,5-a] pyridine-6-methanol and 787 mg (3.48 mmol) of $SnCl_2 \cdot H_2O$ in 40 ml of methanol was heated at reflux for 26 hours. The reaction mixture was then cooled and $H_2S$ was bubbled into the solution. The resulting precipitate was collected by filtration. The filtrate was concentrated and the residue chromatographed on silica gel (95:5:7 CH$_2$Cl$_2$:MeOH:NH$_4$OH) to give 292 mg of product. The hydrochloride salt was prepared with ethanolic HCl in isopropanol, mp. 215-7° C. (dec); [a]$_{25°D}$ =-33° (c =0.219, MeOH).

Analysis: C$_{18}$H$_{27}$N$_3$O$_2$·CHCl·1/2H$_2$O:
Calcd: C, 54,47; H, 7.10; N, 10.57; Cl, 17.84.
Found: C, 54.40; H, 7.11; N, 10.20; Cl, 18.43.

EXAMPLE 13

2-Amino-2-methyl-4-(3-hydroxyphenyl)butane

To a cold (0° C) solution of 482 mg (2.49 mmol) of 2-amino-2-methyl-4-(3-methoxyphenyl)butane in 10 ml of anhydrous methylene chloride, a solution of 3.75 g (14.9) mmol of BBr$_3$ (1.40 ml of 1M solution) in 5 ml of methylene chloride was slowly added. The mixture was stirred at 0° C. for two hours and at room temperature for 4 hours. The reaction mixture was cooled with ice and quenched with MeOH. The mixture was concentrated and then chromatographed on silica gel (95:5:1 CH$_2$Cl$_2$:MeOH:NH$_4$OH) to give 195 mg of amine product.

EXAMPLE 14

(R)-a-[[(1,1-Dimethyl-3-(3-hydroxyphenyl)propyl)amino]methyl]tetrazolo[1,5-a]pyridine-6-methanol A solution of 194 mg (1.21 mmol) of (R)-2-(tetrazolo[1,5-a]pyrid-6-yl)oxirane and 195 mg of 2-amino-2-methyl-4-(3-hydroxyphenyl)butane in 25 ml of absolute ethanol was heated at reflux for 6.5 hours. The reaction mixture was concentrated and the residue chromatographed on silica gel (4:1:2:1 ethyl acetate:n-propanol:water:ammonium hydroxide) to give 137 mg of product.

EXAMPLE 15

(R)-6-Amino-a-[[(1,1-dimethyl-3-(3-hydroxyphenyl)-propyl)amino]methyl]-3-pyridinemethanol Dihydrochloride A solution of 137 mg (0.40 mmol) of (R)-a-[[(1,1-dimethyl-3-(3-hydroxyphenyl)propyl)amino]methyl]-tetrazolo[1,5-a]pyridine-6-methanol and 182 mg (0.81 mmol) of SnCl$_2$·H$_2$O in 20 ml of methanol was heated at reflux for 21 hours. The reaction mixture was cooled in an ice bath and H$_2$S was bubbled through the solution. The precipitate was removed by filtration and the filtrate concentrated. The residue was chromatographed on silica gel (94:6:2 CH$_2$Cl$_2$:MeOH:NH$_4$OH) to give pure product which was converted into its hydrochoride salt with ethanolic HCl, 97.3 mg, [a]$_D$ = -17.3° C.

EXAMPLE 16

2-Amino-2-methyl-4-(2-hydroxyphenyl)butane

To a cold (0° C.) solution of 986 mg (5.1 mmol) of 2-amino-2-methyl-4-(2-methoxyphenyl)butane in 20 ml of dry methylene chloride, a solution of 2.5 ml of a 1M BBr$_3$ solution in 10 ml of methylene chloride is slowly added. The reaction mixture is stirred at 0° C. for two hours and then at room temperature for 3 hours. The reaction is quenched with methanol and concentrated. Pure product may be obtained by chromatography on silica gel.

EXAMPLE 17

(R)-a-[[(1,1-Dimethyl-3-(2-hydroxyphenyl)propyl)amino]methyl]tetrazolo[1,5-a]pyridine-6-methanol A solution of 156 mg (1.46 mmol) of (R)-2-(tetrazolo[1,5-a]pyrid-6-yl)oxirane and 170 ml of 2-amino-2-methyl-4-(2-hydroxyphenyl)butane in 15 ml of absolute ethanol is heated at reflux for 6 hours. The reaction mixture is concentrated and the residue chromatographed on silica gel to give the desired product.

EXAMPLE 18

(R)-6-Amino-a-[[(1,1-dimethyl-3-(2-hydroxyphenyl)-propyl)amino]methyl]-3-pyridinemethanol Dihydrochloride A solution of 127 mg (0.37 mmol) of (R)-a-[[(1,1-dimethyl-3-(2-hydroxyphenyl)propyl)amino]methyl]-tetrazolo[1,5-a]pyridine-6-methanol and 170 mg (0.75 mmol) of SnCl$_2$·2H$_2$O in 15 ml of methanol is heated at reflux for 20 hours. The reaction mixture is cooled in ice and H$_2$S is bubbled through the solution. The precipitate is collected by filtration and the filtrate concentrated. The residue is chromatographed on silica gel to give the desired product.

What is claimed is:

1. A method for the growth promotion and an increase in feed efficiency of animals which comprises administering to an animal an effective amount of a compound having the formula:

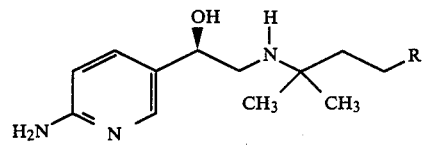

wherein R is:

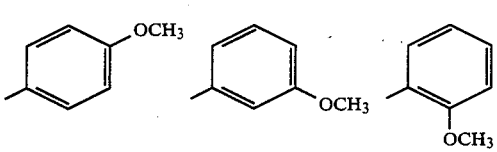

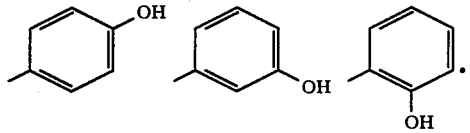

2. The method of claim 1 wherein R is

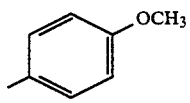

3. The method of claim 1 wherein R is

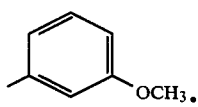

4. The method of claim 1 wherein R is
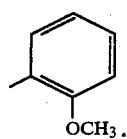
5. The method of claim 1 wherein R is
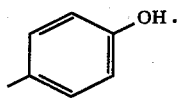
6. The method of claim 1 wherein R is
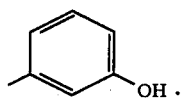
7. The method of claim 1 wherein R is
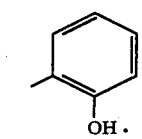
* * * * *